(12) United States Patent
Mrusek et al.

(10) Patent No.: US 6,270,784 B1
(45) Date of Patent: Aug. 7, 2001

(54) ACTIVE SUBSTANCE COMBINATIONS COMPRISING PYRETHROIDS AND INSECT DEVELOPMENT INHIBITORS

(75) Inventors: Klaus Mrusek, Bergisch Gladbach; Manfred-Heinrich Schütte, Dormagen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/011,451

(22) PCT Filed: Aug. 5, 1996

(86) PCT No.: PCT/EP96/03455

§ 371 Date: Feb. 10, 1998

§ 102(e) Date: Feb. 10, 1998

(87) PCT Pub. No.: WO97/06687

PCT Pub. Date: Feb. 27, 1997

(30) Foreign Application Priority Data

Aug. 16, 1995 (DE) ............................... 195 30 075
Feb. 16, 1996 (DE) ............................... 196 05 773

(51) Int. Cl.$^7$ .......................... A01N 53/06; A01N 47/28; A01N 25/00
(52) U.S. Cl. ......................... 424/405; 424/409; 514/531; 514/594
(58) Field of Search .................. 424/405, 409; 514/531, 594

(56) References Cited

U.S. PATENT DOCUMENTS

| | | | | |
|---|---|---|---|---|
| 4,767,773 | * | 8/1988 | Ayad | 514/351 |
| 4,889,872 | * | 12/1989 | Naumann et al. | |
| 5,707,638 | * | 1/1998 | Losel et al. | 424/407 |
| 5,981,596 | * | 11/1999 | Thienpont | 514/594 |
| 5,990,043 | * | 11/1999 | Kugler et al. | 504/116 |
| 6,024,973 | * | 2/2000 | Ishiwatari | 424/416 |
| 6,093,415 | * | 7/2000 | Karr et al. | 424/406 |

FOREIGN PATENT DOCUMENTS

| | | | |
|---|---|---|---|
| 568003 | * | 12/1987 | (AU) . |
| 3317399 | * | 1/1984 | (DE) . |
| 279325 | * | 8/1988 | (EP) . |
| 2122494 | * | 1/1984 | (GB) . |

OTHER PUBLICATIONS

Chemical Abstract 106:115190m.*
W. Behrenz, K. Naumann, Pflanzenschutz–Nachrichten Bayer, 35, 309 (1982).*
C. Fest, K.–J. Schmidt, The Chemistry of Organophosphorus Pesticides, Springer–Verlag, Berlin (1982).*
W. Behrenz, E. Böcker, Pflanzenschutznachrichten Bayer, 18, 53 (1965).*
I. Hammann, R. Fuchs, Pflanzenschutznachrichten Bayer, 34, 123 (1981).*
K. Mrusek in Proc. 1st Int. Conf. Insect Pests in the Urban Environment, Hrsg. K. 1993, 385.*
Chemical Patents Index, Documentation Abstacts Journal, Section CH, Week 9538, Derwent Publications Ltd., London, G.B. Class C03, AN 95–290227 XP002021231 & JP, A, 07 187 922 (Sumitomo Chem. Co. Ltd), Jul. 25, 1995.*

(List continued on next page.)

Primary Examiner—Robert H. Harrison
(74) Attorney, Agent, or Firm—Norris McLaughlin & Marcus P.A.

(57) ABSTRACT

The present invention relates to new active compound combinations of pyrethroids with insect development inhibitors, for achieving a long-term effect against animal pests with high effectiveness, fewer environmentally polluting properties and a toxicologically favourable control concept.

5 Claims, 1 Drawing Sheet

OTHER PUBLICATIONS

Pesticide Science, Bd. 14, nr. 3, Jun. 1983, Barking GB, Seiten 246–252, XP002021224, M.A. El–Guindy, et al.: "The Joint action . . . ".*

Chemical Abstracts, vol. 102, No. 9, Mar. 4, 1985, Columbus, OH, US; Abstract No. 74117q, J.L. Robertson, et al.: "Western spruces budworm: . . . ingestion."*

Chemical Abstracts, vol. 106, No. 15, 13. Apr. 1987, Columbus, OH, US; Abstract No. 115190m, K.A. Kulkarni, et al.: "Effect of synthetic . . . properties."*

Journal of Economic Entomology, Bd. 84, Nr. 6, 1991, College Park, Maryland US, Seiten 1957–1968, XP002021225 G.A. Hughes et al.: "Multinomial logit . . . mixtures."*

* cited by examiner

ACTIVE SUBSTANCE COMBINATIONS COMPRISING PYRETHROIDS AND INSECT DEVELOPMENT INHIBITORS

The present invention relates to new active compound combinations of pyrethroids with insect development inhibitors, for achieving a long-term effect against animal pests, in particular insects and arachnids, having high effectiveness, fewer environmentally polluting properties and a toxicologically favorable control concept.

Combinations of different insecticidal agents have been used for a long time to control insects in interior spaces. In this case, insecticidal compound classes which have no cross-resistances are usually combined with one another. In this manner, formulations are obtained which also have a good action against resistant species (W. Behrenz, K. Naumann, Pflanzenschutz-Nachrichten Bayer, 35, 309 (1982)).

In order to obtain a flushing effect and immediate action ("knock-down action") and long-term action against insects ("residual action"), until now phosphoric acid esters, carbamates and long term-stable pyrethroids were combined with one another (C. Fest, K.-J-. Schmidt, The Chemistry of Organophosphorus Pesticides, Springer-Verlag, Berlin (1982); W. Behrenz, E. Böcker, Pflanzenschutznachrichten Bayer, 18, 53 (1965); I. Hammann, R. Fuchs, ibid. 34, 123 (1981) and references cited there).

Recently, various inhibitors of insect development have been disclosed. These are so-called juvenile hormones and chitin synthesis inhibitors from the benzoylureas class, which specifically affect the development cycle of insects by preventing the conversion of the individual larval stages into the next higher development stages.

This principle of action is specifically suitable to insects and is not found in warm-blooded animals. Besides an extremely effective suppression of the development of new insect generations, the complete absence of side effects on the warm-blooded animals also results from this, whereby a toxicologically favorable control concept is achieved. However, development inhibitors of this type do not have any action on adult stages of insects, so that the action only occurs after a waiting time of up to two weeks. For specific control of pests, in particular insects and arachnids, insecticides must therefore be found which, together with development inhibitors, on the one hand have a flushing effect and an immediate action ("knock-down action"), but on the other hand also persist with a long-term action (residual action) over several development stages of the pests, which is why both active compounds have to be supplemented in an optimum manner.

Surprisingly, it has now been found that by combination of synthetic pyrethroids or natural pyrethrum, which is distinguished as an individual active compound by good knock-down properties and a good flushing effect, but only acts for up to a few days, with insect development inhibitors, a long-term action with excellent effectiveness, fewer environmentally polluting properties and a toxicologically more favourable control concept can be achieved.

BRIEF DESCRIPTION OF THE DRAWINGS

The invention will now be described in greater detail with reference to the drawings, wherein.

Figure 1:
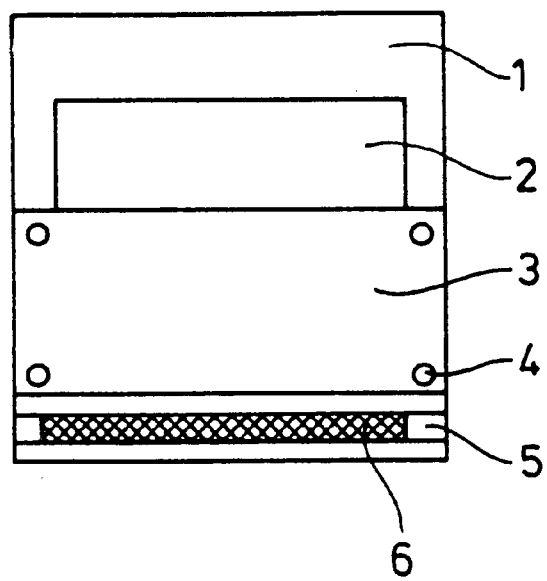
FIG. 1 is a drawing depicting a hiding-place as used in the instant examples.

Pyrethroids preferably employed are pyrethrum, allethrin or transfluthrin, and insect development inhibitors preferably employed are insecticides and chitin synthesis inhibitors, e.g. lufenuron, RH 5849 (2-benzoyl-1-(1,1-dimethylethylbenzoic hydrazide), chlorfluazuron, diflubenzuron, N-[[[3,5-dichloro-4-(4-chlorophenoxy)phenyl]amino]carbonyl]-2,6-difluorobenzamide; flufenoxuron; flucycloxuron; penfluron; teflubenzuron; hexaflumuron; tebufenozide; 2-chloro-N-[[[4-(1-phenylethoxy)-phenyl]-amino]-carbonyl]-benzamide; sodium 1,4-bis-(2-ethylhexyl)-sulphobutanedioate; novaluron, 2-chloro-N-[[[4-(2,2-dichloro-1,1-difluoroethoxy)-phenyl]-amino]-carbonyl]-benzamide; 6-azido-N-cyclopropyl-N'-ethyl-1,3,5-triazine-2,4-diamine; N-[[[5-(4-bromophenyl)-6-methyl-2-pyrazinyl]-amino]-carbonyl]-2,6-dichlorobenzamide; 2,6-dichloro-N-[[( 4-chlorophenyl)amino]-carbonyl]-benzamide; methoprene; triflumuron; pyriproxifen; fenoxycarb.

Particularly preferred active compound combinations consist of transfluthrin, allethrin or pyrethrum on the one hand and of fenoxycarb, pyriproxyfen, triflumuron, flufenoxuron and/or methoprene on the other hand.

Very particularly preferred active compound combinations are those consisting of transfluthrin of the formula (I) and triflumuron of the formula (II) and/or flufenoxuron. The combination of the active compounds combines in an excellent manner outstanding knock-down action and flushing effect with a residual action of over several weeks without a gap in the effect.

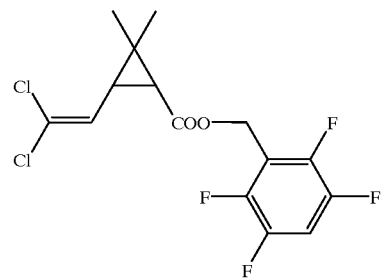

(I)

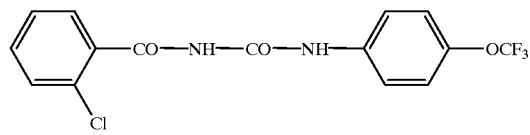

(II)

Furthermore, the active compound combination consisting of transfluthrin of the formula (I) and flufenoxuron (III) in particular surprisingly shows a synergistic effect.

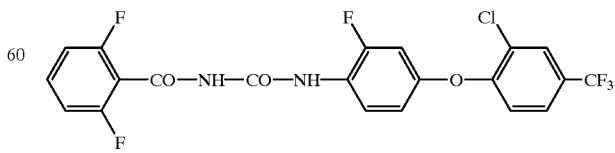

(III)

This effect is characterized in that the characteristic action intrinsic to the transfluthrin is potentiated by addition of flufenoxuron. The addition of flufenoxuron to transfluthrin potentiates both the aerosol effect against flying insects and the effect after direct spraying of cockroaches and the flushing effect. The potentiation of the effect on cockroaches, which is to be observed on freshly sprayed surfaces, is particularly clear.

The active compound combinations according to the invention are suitable for combating animal pests, in particular insects and arachnids, encountered in agriculture, in forestry, in the protection of stored products and of materials, and in the hygiene field. They can preferably be employed as plant protection agents. They are active against normally sensitive and resistant species and against all or some stages of development. The abovementioned pests include:

From the order of the Isopoda, for example, Oniscus asellus, Armadillidium vulgare and Porcellio scaber.

From the order of the Diplopoda, for example, Blaniulus guttulatus.

From the order of the Chilopoda, for example, Geophilus carpophagus and Scutigera spec.

From the order of the Symphyla, for example, Scutigerella immaculata.

From the order of the Thysanura, for example, Lepisma saccharina.

From the order of the Collembola, for example, Onychiurus armatus.

From the order of the Orthoptera, for example, Blatta orientalis, Periplaneta americana, Leucophaea maderae, Blattella germanica, Acheta domesticus, Gryllotalpa spp., Locusta migratoria migratorioides, Melanoplus differentialis and Schistocerca gregaria.

From the order of the Dermaptera, for example, Forficula auricularia.

From the order of the Isoptera, for example, Reticulitermes spp.

From the order of the Anoplura, for example, Pediculus humanus corporis, Haematopinus spp. and Linognathus spp.

From the order of the Mallophaga, for example, Trichodectes spp. and Damalinea spp.

From the order of the Thysanoptera, for example, Hercinothrips femoralis and Thrips tabaci.

From the order of the Heteroptera, for example, Eurygaster spp., Dysdercus intermedius, Piesma quadrata, Cimex lectularius, Rhodnius prolixus and Triatoma spp.

From the order of the Homoptera, for example, Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus spp., Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.

From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrvsorrhoea, Lymantria spp., Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Spodoptera litura, Spodoptera spp., Trichoplusia ni, Carpocapsa pomonella, Pieris spp., Chilo spp., PyTausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana.

From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, G ibbium psylloides, Tribolium spp., Tenebrio molitor, Agriotes spp., Conoderus spp., Melolontha melolontha, Amphimallon solstitialis and Costelytra zealandica.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa.

From the order of the Siphonaptera, for example, Xenopsylla cheopis, Ctentocephalides felis, Ceratophyllus spp.

From the order of the Arachnida, for example, Scorpio maurus, Latrodectus mactans.

From the order of the Acarina, for example, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The active compound combinations according to the invention can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zink.

The active compound combinations according to the invention can be present in their commercially available formulations and in the use forms, prepared from these formulations, as a mixture with other active compounds, such as insecticides, attractants, sterilizing agents, bactericides, acaricides, nematicides, fungicides or growth-regulating substances. The insecticides include, for example, phosphates, carbamates, carboxylates, chlorinated hydrocarbons, phenylureas, substances produced by microorganisms and the like.

The compounds are employed in a customary manner appropriate for the use forms.

The active compound combinations according to the invention can in principle be employed against all flying and crawling insects and arachnids in all stages of development. They are particularly preferably employed in the control of fleas and cockroaches, i.e. insects of the order Blattariae, in particular of the family Blattellidae, preferably of the species Blattella germanica or of the family Blattidae, preferably of the species Blatta orientalis and Periplaneta americana, but also against other cockroach species, but very particularly preferably against Blattella germanica.

Thus, for example, transfluthrin, in addition to its outstanding effect against flying insects, employed in aerosol, vaporizer and fumigant systems, is also a very good agent for flushing insects which live in hiding, e.g. cockroaches in all stages of development, from their hiding-places. These then come into contact with the freshly created active compound coatings and are in this way killed (K. Naumann, W. Behrenz, EP 279 325 (1988)).

If insects, e.g. cockroaches or fleas, are sprayed directly with transfluthrin, these are rapidly knocked down and are not able to recover again (mortality). In order to achieve such effects, the active compound can be employed in all sorts of formulations, e.g. as a spray can, oil spray, water-based pump spray, ULV, hot and cold mist. In addition, suitable formulations are those based on, for example, emulsion concentrates (EC), emulsion concentrates based on water (EW) or wettable powders (WP).

Above and beyond the effect shown, transfluthrin can also be employed as a preparation having a permanent effect for the control of crawling insects, preferably cockroaches but also fleas, if this effect is to be only short, in the sense of a few days. The preparation also acts as a residual active compound used against all stages of development of the cockroaches. For this purpose, for example, spray cans, oil sprays and pump sprays are particularly highly suitable for the non-professional user.

The chitin synthesis inhibitor triflumuron belongs chemically to the benzoylureas group, whose effect differs fundamentally from the conventional insecticides such as phosphates, carbamates or pyrethroids (K. Mrusek in Proc. 1st Int. Conf Insect Pests in the Urban Environment, Ed. K. B. Wildey and W. H. Robinson, 1993, 385).

Triflumuron is not an acute-acting insecticide, but a development inhibitor which specifically intervenes in the skin-shedding process of the various larval stages. As insects have no internal skeleton, an outer skin, the cuticle, fixed by chitin bestows on them the necessary support and external protection. Triflumuron prevents the younger larvae changing into the next higher larval stage during their development. Adult insects, on the other hand, are not adversely affected, because these no longer shed skin. Triflumuron is active in the larvae of many insects, which include cockroaches and fleas.

Chitin only occurs in very specific groups of organisms: besides arthropods also in nematodes, fungi and some algae. In vertebrates, however, it is not present, which explains the extremely favourable low toxicity of triflumuron in vertebrates.

On combined use in practice, the flushing effect, the immediate insecticidal effect on direct spraying of the animals and a short-lasting effect are achieved with transfluthrin in the case of cockroaches. Triflumuron causes the long-lasting effect against the various larval stages.

The active compound content of the use forms prepared from the commercially available formulations can vary within wide limits.

The active compound combinations according to the invention preferably contain 0.001 to 95, particularly preferably 0.01 to 70, % by weight of active compound mixture of both components. A preferred ratio, e.g. in spray cans, is:

0.01–0.2% by weight of transfluthrin:0.005–10.0% by weight of triflumuron or flufenoxuron. Particularly preferred active compound combinations are those having a ratio of 0.01–0.2% by weight of transfluthrin: 0.005–1.5% by weight of triflumuron or flufenoxuron.

Moreover, the active compound combinations according to the invention can, however, also be used in mosquito and fumigating coils, vaporizer plates or long-term vaporizers and also in moth papers, moth pads or other heat-independent vaporizer systems.

In the concept of action, transfluthrin, for example, can also be replaced, however, by pyrethrum and/or allethrin, triflumuron by other chitin synthesis inhibitors, e.g. flufenoxuron, methoprene, or juvenoids, e.g. fenoxycarb, pyriproxvfen.

Besides spray cans, oil sprays and water-based pump sprays, this concept can be used for the control of pests in other formulations, too, e.g. ULV, hot and cold mist, and emulsion concentrates (EC), emulsion concentrates based on water (EW), wettable powders (WP) or microencapsulations (CS).

Preferably, aerosols or oil sprays are employed. Aerosol recipes are preferably composed of the active compound combinations mentioned, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methyl-pyrrolidone, dimethyl sulphoxide, aromatic hydrocarbons such as toluene, xylene, water, furthermore auxiliaries such as emulsifiers such as sorbitan monooleate, oleyl ethoxylate having 3–7 mol of ethylene oxide, fatty alcohol etho.xylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

In the case of spray cans, the aerosol mixture as a whole is in a suitable, adequately pressure-resistant packing. The material ofthis packing can be metal (galvanized iron or aluminium) with or without a separate internal protective coating, and furthermore glass, with or without a plastic covering, and certain plastics are suitable (e.g. polyamide, polypropylene, PET).

The aerosol packing includes a suitable, automatically closing valve having physicotechnical parameters optimized for the use, such as nozzle openings, nozzle type, sealing materials etc. To ensure against unintentional operation of the valve, the aerosol packing is preferably to be provided with a suitable protective cap.

The oil spray formulations differ fundamentally from the aerosol recipes in that no propellants are used, since as a rule mechanical pumps are provided for atomization. The solvents and other auxiliaries used virtually do not differ from the compositions customary in aerosol recipes. The packing material for these formulations is far less critical, as fundamentally only imperviousness and resistance to the filling material are demanded. Thus, for example, metals such as iron, mainly galvanized and/or coated, aluminium etc. are suitable. Glass and certain plastics such as polyvinyl chloride, polyethylene, polypropylene and PET are further suitable.

The selection of the particular solvents and other additives and also the type of the spray cans and of the packing depends on the available materials, on the specific areas of use and on the demands on the storability of the products and can be easily made by the person skilled in the art using his expert knowledge and, if appropriate, with the aid of simple., generally known investigation methods.

The preparation of the active compound combinations according to the invention will be explained with the aid of the following examples.

FORMULATION EXAMPLES

| 1. | Spray formulation | Parts by weight |
|---|---|---|
| | Transfluthrin | 0.05 |
| | Triflumuron | 0.5 |
| | Acetone | 40.0 |
| | Deodorized kerosene/mixture of saturated, aliphatic hydrocarbons (e.g. isododecane) | 19.32 |

-continued

| 1. | Spray formulation | Parts by weight |
|---|---|---|
| | Perfume oil | 0.03 |
| | Stabilizer (butylene oxide, triethyl orthoformate) | 0.1 |
| | Propellant: propane/butane (25:75) | 40.00 |

| 2. | Spray formulation | Parts by weight |
|---|---|---|
| | Pyrethrins | 0.20 |
| | Triflumuron | 0.5 |
| | Acetone | 40.0 |
| | Deodorized kerosene | 19.197 |
| | Perfume oil | 0.003 |
| | Stabilizer (as Example 1) | 0.1 |
| | Propellant: propane/butane (25:75) | 40.00 |

| 3. | Spray formulation | Parts by weight |
|---|---|---|
| | Transfluthrin | 0.03 |
| | Flufenoxuron | 0.05 |
| | Isopropanol | 5.00 |
| | Deodorized kerosene | 5.00 |
| | Emulsifier Span 80 | 1.00 |
| | Water, demineralized | 58.92 |
| | Propellant: propane/butane (25:75) | 30.0 |

| 4. | Oil spray formulation | Parts by weight |
|---|---|---|
| | Transfluthrin | 0.03 |
| | Triflumuron | 0.5 |
| | N-Methylpyrrolidone | 20.0 |
| | Deodorized kerosene | 79.20 |

| 5. | Oil spray formulation | Parts by weight |
|---|---|---|
| | Pyrethrins | 0.2 |
| | Triflumuron | 0.5 |
| | N-Methylpyrrolidone | 20.0 |
| | Deodorized kerosene | 79.30 |

Testing of Spray Cans for Flushing Effect on Cockroaches

Testing was carried out in plastic trays (pricking-out boxes, type 23, W. and H. Fernholz GmbH & Co. KG, Meinerzhagen) measuring 40 cm×60 cm×6 cm. The filter paper laid on the bottom was fixed with "tesa"® film 4104. Talcumed side walls prevented the escape of the cockroaches. The hiding-place was set up in the centre of the trays, and an inverted water-filled weighing glass as a drinking place and a piece of rusk as food in the front third.

The bottom and covering sheet of the hiding-place consist of aluminum coated with white DD lacquer, the side bars and slide of Teflon. Countersunk bolts and wing nuts hold the construction together, the desired hiding-place depth being adjusted by means of the slide. The construction and dimensions of the hiding-place can be seen from FIG. 1: [1=bottom plate 15×30×0.5 cm, 2=slide 13×16×0.5 cm, 3=covering plate 15×15×0.5 cm, 4=countersunk bolt with wing nut, 5=side bar 1×16×0.5 cm, 6=opening]. The hiding-place height can be varied by exchanging the slide and the side bars.

24 hours before the start of the experiment, 10 cockroaches of a certain species and stage or sex were inserted in each container. After this time, as a rule, all animals were found in the hiding-place. This was transferred to the fume cupboard and placed in a plastic container measuring 65 cm×46.5 cm×30 cm on two glass cylinders (total height 36 cm, diameter 12 cm). 2 g of can contents were sprayed in the direction of the hiding-place opening from a distance of 30 cm and 36 cm height.

After completion of the spraying operation, the hiding-place in the plastic tray was transferred to a talcumed glass ring (height 5 cm, diameter 10 cm). The number of flushed cockroaches was determined up to 5 min. after treatment in one-minute intervals and up to 30 min in five-minute intervals, and also after 60 min. and 24 hours. After 60 min., a folded filter disc of diameter 9.5 cm was added to the pricking-out boxes as protection for the flushed cockroaches. In each experiment, a control treatment was carried out using an active compound-free can. Only in isolated cases did the flushed-out cockroaches seek out the hiding-place again; as a rule, they soon fell off the hiding-place. After conclusion of the experiment, the hiding-places were unscrewed, washed with acetone, cleaned at 95° C. in a dishwasher and dried at 150° C. in a drying oven.

Before and after each experiment, the can is weighed in order to determine the amount applied exactly. Simultaneously to the spray valve, a stop clock is actuated in order to be able to determine the knock-down effect on the animals exactly. The animals are transferred to a clean container immediately after spraying, provided with a swab and assessed after certain times for knock-down after time and also % mortality.

TABLE 2

Effect of various spray cans after direct spraying of cockroaches of the species *Blattella germanica* mm
Spray quantity: 2.4–2.8 g of can contents/cockroach from a distance of 60 cm
Temperature: 22° C.
rel. humidity: 47%
(Average of 10 experiments)

| % active compound | | % knock-down after seconds ("): | | | % mortality after: | | |
|---|---|---|---|---|---|---|---|
| Trans-fluthrin | Triflumuron | Average | Scatter width | | 2 h | 24 h | 48 h |
| 0.05 | — | 33" | 19"–58" | | 100 | 100 | 90 |
| — | 0.5 | — | — | | 0 | 10 | 10 |
| 0.05 | 0.5 | 27" | 14"–55" | | 100 | 100 | 100 |

TABLE 1

Flushing effect of various spray cans against cockroaches of the species *Blattella germanica* L 5
Hiding-place height: 0.5 cm    Average of two experiments    Temperature: 21° C.
Hiding-plate depth: 5.0 cm    rel. humidity: 55%
Spray quantity: 2.0–2.2 g of can contents

| % active compound | | % flushing effect after minutes (') and hours (h) | | | | | | | | | | | |
|---|---|---|---|---|---|---|---|---|---|---|---|---|---|
| Trans-fluthrin | Triflumuron | 1' | 2' | 3' | 4' | 5' | 10' | 15' | 20' | 25' | 30' | 60' | 24 h |
| 0.05 | — | 45 | 60 | 70 | 85 | 85 | 100 | 100 | 100 | 100 | 100 | 100 | 100 |
| — | 0.5 | 0 | 0 | 0 | 0 | 0 | 0 | 0 | 0 | 0 | 0 | 0 | 20 |
| 0.05 | 0.5 | 20 | 30 | 55 | 65 | 70 | 95 | 95 | 95 | 95 | 95 | 95 | 95 |
| — | — | 0 | 0 | 0 | 0 | 0 | 0 | 0 | 0 | 0 | 0 | 0 | 20 |

Testing of Spray Cans for Effect after Direct Spraying of Crawling Insects

The experiments are carried out in a fume cupboard in which the suction can be regulated such that an adverse effect on the spray jet does not take place. One cockroach in each case is placed in a wire gauze box having an internal diameter of 70 mm, a height of 10 mm and a mesh width of 1.5 mm. The experimental containers prepared in this way are inserted into the spray apparatus at an angle of 45°. The area behind and under the gauze test container is lined with absorbent filter paper, which is replaced after each test.

At a distance of 60 cm calculated from the centre of the wire gauze to the nozzle of the spray head of the aerosols to be tested, the spray can is inserted into the spray apparatus such that the spray jet impinges vertically on the wire gauze. The time is determined beforehand for which spraying must be carried out in order to apply 2.4–2.8 g of can contents from the can to be tested.

Test Method for Checking Spray Cans for their Residual Effect Against Crawling Insects 1. Spraying of the Substrates The treatment is carried out in a fume cupboard in which the suction is regulated such that an adverse effect of the spray jet of the cans does not take place. The cupboard is lined on the bottom and on the walls up to a height of 65 cm with filter paper.

The most important materials, in particular glazed and unglazed tiles, PVC sheets, varnished plywood etc., can be treated. The substrates to be treated (size 15×15 cm=225 $cm^2$) are mounted on a stand ring (external diameter 10 cm), which is fixed to a stand at a height of 5 cm, and leant on the stand rod such that an angle of 55° is formed. As each spray can of different composition and technical finishing can differ in its spray behaviour (pressure, spray cone, droplet size), the person who conducts the experiment, before the actual substrates are treated, must practise with each spray can on cardboard substrates (15×15 cm) from what distance and at what speed spraying must be carried out.

Figure 2:
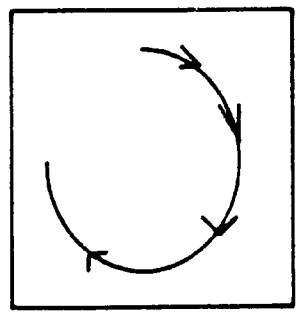
FIG. 2 is a drawing depicting the manner in which the substrates are to be sprayed with the test compositions according to the instant examples.

An even spraying of the substrates at the desired application rate is achieved when, depending on the spray cone and pressure of the spray can, spraying is carried out from a distance of 25–40 cm. It has proved expedient here to guide the can by hand in a semicircle. The spray jet is in this case guided onto the substrate beginning at the top on the left over the center to the right and downwards to the left (FIG. 2).

The amount which is sprayed beyond the edges of the substrates, the spray loss, was determined in detailed experiments using cardboard borders and was about 10%.

Before and after each spray operation, the spray can is weighed in order to determine the quantity of can contents applied.

In order to apply a quantity of can contents of 50 g/m$^2$, 1.24 g of can contents/225 cm$^2$ must be applied. This quantity already contains the 10% spray loss determined.

Substrates to which the quantity of can contents lying within the tolerance from 1.20 to 1.30 g are not applied must be discarded. Immediately after spraying, the substrate is taken from its slanting position and laid flat in order to avoid running-off of the spray coating, in particular with non-absorbent substrates and extremely wet spray cans. After the spray coatings have dried off, the substrates are transferred to the test room.

2. Animal Material and Testing

The treated substrates are populated with 5 cockroaches each, which are kept in talcumed glass rings (diameter 9.5 cm, height 5.5 cm).

Assessment:

One day after the treatment, then daily after 2 to 4 days, the treated substrates are in each case populated with the test animals.

Assessment is carried out for 100% knock-down and mortality after 15, 30 and 60 minutes and also after 2, 3 and 4 hours.

TABLE 3

Residual effect of various spray cans applied to glazed tiles (GT) and unglazed tiles (UT) against cockroaches of the species *Blattella germanica* mm.
Temperature: 24–25° C.
rel. humidity: 69–76%

| Age of the substrates | Test period | 0.05% Transfluthrin | | 0.5% Triflumuron | | 0.05% Transfluthrin 0.5% Triflumuron | | Control | |
|---|---|---|---|---|---|---|---|---|---|
| | | GT | UT | GT | UT | GT | UT | GT | UT |
| 1st day | 15' | 80 | 0 | 0 | 0 | 20 | 40 | 0 | 0 |
| | 30' | 100 | 80 | 0 | 0 | 100 | 100 | 0 | 0 |
| | 60' | 100 | 100 | 0 | 0 | 100 | 100 | 0 | 0 |
| | 2 h | 100 | 100 | 0 | 0 | 100 | 100 | 0 | 0 |
| 2 days | 3 h | 100 | 100 | 0 | 0 | 100 | 100 | 0 | 0 |
| | 4 h | 100 | 100 | 0 | 0 | 100 | 100 | 0 | 0 |
| | 15' | 100 | 20 | 0 | 0 | 100 | 20 | 0 | 0 |
| | 30' | 100 | 60 | 0 | 0 | 100 | 80 | 0 | 0 |
| | 60' | 100 | 60 | 0 | 0 | 100 | 100 | 0 | 0 |
| | 2 h | 100 | 100 | 0 | 0 | 100 | 100 | 0 | 0 |
| | 3 h | 100 | 100 | 0 | 0 | 100 | 100 | 0 | 0 |
| | 4 h | 100 | 100 | 0 | 0 | 100 | 100 | 0 | 0 |
| 3 days | 15' | 0 | 0 | 0 | 0 | 60 | 20 | 0 | 0 |
| | 30' | 100 | 0 | 0 | 0 | 80 | 60 | 0 | 0 |
| | 60' | 100 | 40 | 0 | 0 | 100 | 100 | 0 | 0 |
| | 2 h | 100 | 20 | 0 | 0 | 100 | 80 | 0 | 0 |
| | 3 h | 100 | 40 | 0 | 0 | 100 | 100 | 0 | 0 |
| | 4 h | 100 | 40 | 0 | 0 | 100 | 100 | 0 | 0 |
| 4 days | 15' | 20 | 0 | 0 | 0 | 20 | 20 | 0 | 0 |
| | 30' | 20 | 0 | 0 | 0 | 20 | 20 | 0 | 0 |
| | 60' | 20 | 0 | 0 | 0 | 40 | 20 | 0 | 0 |
| | 2 h | 40 | 0 | 0 | 0 | 20 | 20 | 0 | 0 |
| | 3 h | 40 | 0 | 0 | 0 | 20 | 20 | 0 | 0 |
| | 4 h | 60 | 0 | 0 | 0 | 20 | 20 | 0 | 0 |

Forced Contact Time Test 5 larvae of the cockroach species Blattella germanica of a defined stage are in each case placed onto the substrates to be tested within talcumed glass ring (diameter 9.5 cm; height 5.5 cm). By removing the animals after certain times, different contact times can be achieved, e.g. 2×60 min./week (Tuesday and Friday). The larvae are taken from the surfaces, in each case transferred to transparent plastic beakers in which there are water, food and a hiding-place (tablet tubes of diameter 1.5 cm, length 5.5 cm filled with wet cellulose, Lupolen stoppers with 425 mg of ground dog oiscuits, filter paper of diameter 7 cm folded 3 times as a hiding-place) and raised further therein. The cockroaches are assessed for mortality at weekly intervals. The temperatures are 22–23° C., the rel. atmospheric humidity 55–65% with a 12-hour neon light day/night rhythm.

The tests were carried on one day-old surfaces as well as surfaces aged for 8, 15, 22, 29, 43, 57, 85 and 113 days.

TABLE 4

Residual effect of transfluthrin and triflumuron alone and in combination in spray cans on glazed tiles against the 2nd larval stage of *Blattella germanica*
(Average of 2 experiments)
Temperature: 22–23° C.
rel. humidity: 55–65%
Spray quantity: 50 g of can contents/m$^2$
Contact time: 2 × 1 hour/week

| Age of the substrates | Test period | 0.05% Transfluthrin | 0.5% Triflumuron | 0.05% Transfluthrin 0.5% Triflumuron | Control |
|---|---|---|---|---|---|
| 1st day | 15' | 100 | 0 | 100 | 0 |
| | 30' | | 0 | | 0 |

TABLE 4-continued

Residual effect of transfluthrin and triflumuron alone and in combination in
spray cans on glazed tiles against the 2nd larval stage of Blattella germanica
(Average of 2 experiments)
Temperature: 22–23° C.
rel. humidity: 55–65%
Spray quantity: 50 g of can contents/m$^2$
Contact time: 2 × 1 hour/week

| Age of the substrates | Test period | 0.05% Transfluthrin | 0.5% Triflumuron | 0.05% Transfluthrin 0.5% Triflumuron | Control |
|---|---|---|---|---|---|
| | 60' | | 0 | | 0 |
| | 4 d | | 20 | | 20 |
| | 7 d | | 30 | | 20 |
| | 11 d | | 70 | | 20 |
| | 14 d | | 80 | | 20 |
| | 18 d | | 90 | | 20 |
| | 21 d | | 90 | | 20 |
| | 25 d | | 100 | | 20 |
| 8 days | 4 d | 0 | 50 | 60 | 0 |
| | 7 d | 10 | 80 | 80 | 0 |
| | 11 d | 30 | 80 | 80 | 0 |
| | 14 d | 30 | 90 | 90 | 0 |
| | 18 d | 30 | 100 | 90 | 20 |
| | 21 d | 30 | | 100 | 20 |
| | 25 d | 30 | | | 20 |
| | 32 d | 30 | | | 20 |
| | 35 d | 40 | | | 20 |
| 15 days | 4 d | 0 | 20 | 10 | 0 |
| | 7 d | 10 | 40 | 30 | 0 |
| | 11 d | 10 | 80 | 90 | 0 |
| | 14 d | 10 | 80 | 100 | 0 |
| | 18 d | 10 | 90 | | 0 |
| | 21 d | 10 | 100 | | 0 |
| 22 days | 4 d | 0 | 60 | 40 | 0 |
| | 7 d | 0 | 60 | 80 | 0 |
| | 11 d | 0 | 100 | 90 | 0 |
| | 14 d | 0 | | 100 | 0 |
| 29 days | 4 d | | 10 | 0 | 0 |
| | 7 d | | 20 | 30 | 0 |
| | 11 d | | 70 | 60 | 0 |
| | 14 d | | 70 | 90 | 0 |
| | 18 d | | 80 | 90 | 0 |
| | 21 d | | 100 | 100 | 0 |
| 43 days | 4 d | | 0 | 0 | 0 |
| | 7 d | | 10 | 50 | 0 |
| | 11 d | | 80 | 80 | 0 |
| | 14 d | | 80 | 80 | 0 |
| | 18 d | | 90 | 100 | 0 |
| | 21 d | | 100 | | 0 |
| §7 days | 4 d | | 0 | 10 | 0 |
| | 7 d | | 40 | 60 | 0 |
| | 11 d | | 80 | 80 | 0 |
| | 14 d | | 100 | 90 | 0 |
| | 18 d | | | 90 | 0 |
| | 21 d | | | 90 | 20 |
| | 25 d | | | 90 | 20 |
| | 31 d | | | 90 | 20 |
| | 38 d | | | 100 | 20 |
| 85 days | 4 d | | 10 | 0 | 0 |
| | 7 d | | 50 | 60 | 0 |
| | 11 d | | 60 | 70 | 0 |
| | 14 d | | 100 | 90 | 0 |
| | 18 d | | | 100 | |
| 113 days | 4 d | | 0 | 0 | 0 |
| | 7 d | | 10 | 0 | 0 |
| | 11 d | | 30 | 30 | 0 |
| | 14 d | | 90 | 100 | 0 |
| | 18 d | | 100 | | |

TABLE 5

Residual effect of transfluthrin and triflumuron alone and in combination in spray cans on glazed tiles against the 3rd–4th larval stage of Blattella germanica (Average of 2 experiments)
Temperature: 22–23° C.
rel. humidity: 55–65%
Spray quantity: 50 g of can contents/m$^2$
Contact time: 2 × 1 hour/week

| Age of the substrates | Test period | 0.05% Transfluthrin | 0.5% Triflumuron | 0.05% Transfluthrin 0.5% Triflumuron | Control |
|---|---|---|---|---|---|
| 1st day | 15' | 100 | 0 | 100 | 0 |
|  | 30' | 100 | 0 | 100 | 0 |
|  | 60' | 100 | 0 | 100 | 0 |
|  | 4 d | 80 | 0 | 30 | 0 |
|  | 7 d | 80 | 10 | 30 | 0 |
|  | 11 d | 80 | 60 | 30 | 0 |
|  | 14 d | 80 | 90 | 100 | 0 |
|  | 18 d | 80 | 100 |  | 0 |
| 8 days | 4 d | 20 | 10 | 10 | 0 |
|  | 7 d | 20 | 60 | 50 | 0 |
|  | 11 d | 20 | 90 | 50 | 0 |
|  | 14 d | 20 | 100 | 80 | 0 |
|  | 18 d | 20 |  | 100 | 0 |
| 15 days | 4 d | 0 | 10 | 10 | 0 |
|  | 7 d | 0 | 10 | 20 | 0 |
|  | 11 d | 0 | 20 | 60 | 0 |
|  | 14 d | 0 | 70 | 70 | 0 |
|  | 25 d | 0 | 70 | 80 | 0 |
|  | 35 d | 0 | 80 | 90 | 0 |
|  | 39 d | 0 | 90 | 100 | 20 |
|  | 53 d | 0 | 100 |  | 20 |
| 22 days | 4 d | 0 | 20 | 30 | 0 |
|  | 7 d | 0 | 40 | 50 | 0 |
|  | 11 d | 0 | 60 | 60 | 0 |
|  | 14 d | 0 | 60 | 70 | 0 |
|  | 18 d | 0 | 90 | 70 | 0 |
|  | 21 d | 0 | 100 | 70 | 0 |
|  | 28 d | 10 |  | 70 | 0 |
|  | 35 d | 10 |  | 80 | 0 |
|  | 39 d | 10 |  | 90 | 0 |
|  | 66 d | 10 |  | 100 | 20 |
| 29 days | 4 d |  | 10 | 0 | 0 |
|  | 7 d |  | 60 | 30 | 0 |
|  | 11 d |  | 80 | 60 | 0 |
|  | 14 d |  | 80 | 90 | 0 |
|  | 18 d |  | 90 | 90 | 0 |
|  | 21 d |  | 90 | 100 | 0 |
|  | 25 d |  | 100 |  | 0 |
| 43 days | 4 d |  | 10 | 10 | 0 |
|  | 7 d |  | 20 | 20 | 0 |
|  | 11 d |  | 40 | 40 | 0 |
|  | 14 d |  | 60 | 50 | 0 |
|  | 18 d |  | 80 | 60 | 0 |
|  | 21 d |  | 100 | 60 | 0 |
|  | 32 d |  |  | 70 | 0 |
|  | 35 d |  |  | 80 | 0 |
|  | 45 d |  |  | 90 | 0 |
|  | 52 d |  |  | 100 | 0 |
| 57 days | 4 d |  | 0 | 0 | 0 |
|  | 7 d |  | 0 | 20 | 0 |
|  | 11 d |  | 0 | 20 | 0 |
|  | 14 d |  | 70 | 50 | 0 |
|  | 18 d |  | 90 | 70 | 0 |
|  | 21 d |  | 90 | 80 | 0 |
|  | 25 d |  | 90 | 90 | 0 |
|  | 60 d |  | 100 | 90 | 0 |
|  | 64 d |  |  | 100 | 0 |
| 85 days | 4 d |  | 0 | 30 | 0 |
|  | 7 d |  | 50 | 70 | 0 |
|  | 11 d |  | 60 | 70 | 0 |
|  | 14 d |  | 70 | 70 | 0 |
|  | 18 d |  | 80 | 90 | 0 |
|  | 21 d |  | 90 | 100 | 0 |
|  | 28 d |  | 100 |  | 0 |
| 113 days | 4 d |  | 30 | 10 | 0 |
|  | 7 d |  | 50 | 10 | 0 |
|  | 11 d |  | 60 | 10 | 0 |

TABLE 5-continued

Residual effect of transfluthrin and triflumuron alone and in combination in spray cans on glazed tiles against the 3rd–4th larval stage of *Blattella germanica*
(Average of 2 experiments)
Temperature: 22–23° C.
rel. humidity: 55–65%
Spray quantity: 50 g of can contents/m$^2$
Contact time: 2 × 1 hour/week

| Age of the substrates | Test period | 0.05% Transfluthrin | 0.5% Triflumuron | 0.05% Transfluthrin 0.5% Triflumuron | Control |
|---|---|---|---|---|---|
| | 14 d | | 70 | 30 | 0 |
| | 18 d | | 70 | 80 | 0 |
| | 25 d | | 90 | 80 | 0 |
| | 28 d | | 90 | 90 | 0 |
| | 45 d | | 90 | 100 | 0 |
| | 49 d | | 100 | | 0 |

TABLE 6

Synergistic potentiation of the flushing effect with various formulations against cockroaches of the species *Blattella germanica* L 5
Hiding-place height: 0.5 cm    Average of three experiments
Hiding-place depth: 5.0 cm    Temperature 21° C.
Relative humidity: 48%
Spray quantity: 1.9–2.0 g of can contents

| % active compound | | % flushing effect after minutes and hours | | | | | | | | | | | |
|---|---|---|---|---|---|---|---|---|---|---|---|---|---|
| Trans-fluthrin | Flufen-oxuron | 1' | 2' | 3' | 4' | 5' | 10' | 15' | 20' | 25' | 30' | 60' | 24 h |
| — | 0.01 | 7 | 17 | 17 | 17 | 17 | 17 | 17 | 17 | 17 | 17 | 27 | 87 |
| 0.05 | — | 13 | 13 | 20 | 27 | 37 | 63 | 73 | 73 | 77 | 77 | 77 | 97 |
| 0.05 | 0.01 | 23 | 37 | 47 | 53 | 67 | 80 | 80 | 87 | 87 | 87 | 87 | 93 |
| 0.05 | 0.0025 | 37 | 50 | 60 | 63 | 83 | 90 | 90 | 93 | 97 | 97 | 97 | 100 |
| — | — | 0 | 0 | 0 | 0 | 0 | 0 | 0 | 0 | 0 | 0 | 0 | 83 |

At both hiding-place depths, the results showed that flufenoxuron as a monospray can caused only a slight irritation with the cockroaches. The combination of transfluthrin +flufenoxuron in the water-based spray cans, however, resulted in a distinctly better flushing effect than the transfluthrin monospray can.

At all 3 concentrations, flufenoxuron alone showed no action on the cockroaches. In all 3 combinations, transfluthrin in combination with flufenoxuron showed a distinct improvement in the action in comparison with transfluthrin alone. With increasing flufenoxuron content, the effect improved so that the combination had a better effect by the factor 2–2.5 times than the monospray can.

TABLE 7

Synergistic potentiation of the activity of various spray cans after direct spraying of cockroaches of the species *Blattella germanica* L 5.
Spray quantity: 2.4–2.8 g of can contents/cockroach from a distance of 60 cm
Temperature: 20° C.
Relative humidity: 50%    (Average of 10 experiments)

| % active compound | | 100% knock-down after minutes (') and seconds (") | | % mortality after | | |
|---|---|---|---|---|---|---|
| Trans-fluthrin | Flufen-oxuron | mean | range | 2 h | 24 h | 48 h |
| — | 0.01 | >2 h | — | 0 | 0 | 0 |
| — | 0.005 | >2 h | — | 0 | 0 | 0 |
| — | 0.0025 | >2 h | — | 0 | 0 | 0 |
| 0.05 | — | 166" | 61"–335" | 100 | 50 | 30 |
| 0.05 | 0.01 | 52" | 21"–89" | 100 | 100 | 100 |
| 0.05 | 0.005 | 60" | 16"–150" | 100 | 100 | 90 |
| 0.05 | 0.0025 | 78" | 16"–140" | 100 | 100 | 80 |

TABLE 8

Synergistic potentiation of the activity of various aerosol spray cans in 20 m$^3$ chambers against mosquitoes of the species *Culex quinquefasciatus*, resistant.
(Average of 3–5 experiments)
Room temperature: 23.6–24.2° C.
Spray quantity/20 m$^3$: 8.7–9.1 g
Relative humidity: 44.9–64.3%
Spray time: 4.3–9.1 s

| % active compound | | % knock-down after minutes and seconds | | | 24 h | |
|---|---|---|---|---|---|---|
| Trans-fluthrin | Flufen-oxuron | KT 10 | KT 50 | KT 95 | 1h-Kd [%] | mortality [%] |
| — | 0.010 | — | — | — | 0 | 0 |
| 0.050 | — | 9.53 | 12.30 | 23.39 | 99 | 93 |
| 0.050 | 0.010 | 8.49 | 11.27 | 19.59 | 100 | 97 |
| 0.050 | 0.005 | 8.36 | 11.57 | 19.07 | 100 | 96 |
| 0.050 | 0.0025 | 7.41 | 10.33 | 19.29 | 99 | 96 |

TABLE 9

Synergistic potentiation of the activity of various aerosol spray
cans in 20 m³ chambers against flies of the species
*Musca domestica* strain WHO(N) mm F 447, sensitive
(Average of 3–5 experiments)
Room temperature: 23.6–24.2° C.
relative humidity: 44.9–64.3%
Spray quantity/20 m³: 8.7–9.1 g
Spray time: 4.3–9.1 s

| % active compound | | knock-down after minutes and seconds | | | 1h-KD | 24 h mortality |
|---|---|---|---|---|---|---|
| Trans-fluthrin | Flufen-oxuron | KT 10 | KT 50 | KT 95 | [%] | [%] |
| — | 0.010 | — | — | — | 0 | 0 |
| 0.050 | — | 11.58 | 21.00 | 36.00 | 98 | 76 |
| 0.050 | 0.010 | 10.14 | 15.08 | 25.23 | 100 | 79 |
| 0.050 | 0.005 | 9.41 | 15.31 | 24.56 | 100 | 87 |
| 0.050 | 0.0025 | 10.17 | 16.19 | 23.50 | 100 | 90 |

TABLE 10

Synergistic potentiation of the activity of various aerosol spray
cans in 20 m³ chambers against flies of the species
*Musca domestica* strain Weymanns mm F 386, resistant.
(Average of 3–5 experiments)
Temperature: 23.5–24.2° C.
Relative humidity: 40.5–65.3%
Spray quantity/20 m³: 11.7–12.0 g
Spray time: 6.2–12.1 s

| % active compound | | % knock-down after minutes and seconds | | | 1h-KD | 24 h mortality |
|---|---|---|---|---|---|---|
| Trans-fluthrin | Flufen-oxuron | KT-10 | KT-50 | KT-95 | [%] | [%] |
| — | 0.010 | — | — | — | 0 | 0 |
| 0.050 | — | 47.23 | — | — | 43 | 15 |
| 0.050 | 0.010 | 36.57 | 50.44 | — | 69 | 43 |
| 0.050 | 0.005 | 30.58 | 46.11 | — | 77 | 31 |
| 0.050 | 0.0025 | 37.15 | 54.13 | — | 63 | 35 |

This can containing 0.01% flufenoxuron, as to be expected, showed no effect in all the animal species tested.

The combination cans acted distinctly more rapidly against the resistant mosquitoes than the transfluthrin mono-can (Table 8).

In the sensitive and resistant flies, the combination cans acted more rapidly than the transfluthrin mono-can. This difference made itself particularly distinctly noticeable in the mortality for resistant flies (Tables 9–10).

Testing of Spray Cans for Effect of Fresh Still-Wet Spray Coatings Against Cockroaches.

1. Spraying of the Substrates

The spraying is carried out in a fume cupboard in which the suction is regulated such that an adverse effect on the spray jet of the cans does not take place. The cupboard is lined on the bottom with filter paper.

The most important materials can be treated, in particular glazed and unglazed tiles, PVC sheets, varnished plywood etc. The substrates to be treated (size 15×15 cm=225 cm²) are put into a spray box lined with filter paper, an aspirated container which is open to the front, in a holder at an angle of 45° C. As each spray can of different composition and technical finishing can differ in its spray behaviour (pressure, spray cone, droplet size), the person who conducts the experiment, before the actual substrates are treated, must practise with each spray can on cardboard substrates (15×15 cm) from what distance and at what speed spraying must be carried out.

An even spraying of the substrates at the desired application rate is achieved when, depending on the spray cone and pressure of the spray can, spraying is carried out from a distance of 25–40 cm. It has proved expedient here to guide the can by hand in a semicircle. The spray jet is in this case guided onto the substrate beginning at the top on the left over the centre to the right and downwards to the left (see FIG. 2).

The amount which is sprayed beyond the edges of the substrates, the spray loss, was determined in detailed experiments with cardboard borders and was about 10%.

Before and after each spray operation, the spray can is weighed in order to determine the quantity of can contents applied.

In order to apply a, for example, can contents quantity of 25 g/m², 0.64 g of can contents/225 cm² must be applied. This quantity already contains the 10% spray loss determined.

Substrates to which the quantity of can contents lying within the tolerance of 0.59 to 0.69 g is not applied must be discarded. Immediately after the spraying, the substrate is taken from its slanting position and laid flat in order to avoid running-off of the spray coating, in particular with non-absorbent substrates and extremely wet spray cans. After the spray coatings have dried off, the substrates are transferred to the test room.

2. Animal Material and Testing

The freshly treated still-wet substrates are populated with the test animals (cockroaches).

The test animals are kept on the substrates in talcumed glass rings (diameter 9.5 cm, height 5.5 cm). In the case of test animals which can get over the height of the glass ring, accordingly rings are placed one on the other. Depending on the size, 5 to 10 animals are employed per substrate. Fleas are kept in non-talcumed glass rings.

In the case of the cockroaches, the species Blattella germanica and Blatta orientalis are employed.

3. Assessment

Assessment is carried out for 20 and 100% knock-down after seconds or minutes for up to 2 hours. Assessment is then made as a percentage.

TABLE 11

Synergistic potentiation of the activity of spray cans, measured
on various still-wet surfaces against cockroaches
of the species *Blattella germanica* L.5.
Temperature: 21° C.   Relative humidity: 48%
Spray quantity: 25 g/m²

| % active compound | | 20/100% knock-down after minutes (') and seconds (") | | |
|---|---|---|---|---|
| Transfluthrin | Flu-fenoxuron | PVD | glazed tiles | unglazed tiles |
| — | 0.01 | 2 h 0% | 2 h 0% | 2 h 0% |
| 0.05 | — | 35"/5'00" | 1'10"/3'40" | 50"/2'10" |
| 0.05 | 0.01 | 25"/3'50 | 10"/40" | 40"/2'00" |
| 0.05 | 0.005 | 35"/5'00" | 40"/1'50" | 1'00"/1'50" |
| 0.05 | 0.0025 | 15"/1'10" | 25"/1'00" | 15"/1'40" |
| — | — | 2 h 0% | 2 h 0% | 2 h 0% |

TABLE 12

Synergistic potentiation of the activity of spray cans, measured on various still-wet surfaces against cockroaches of the species *Blatta orientalis* L 5.
Temperature: 21° C. Relative humidity: 48%
Spray quantity: 25 $g/m^2$

| % active compound | | 20/100% knock-down after minutes (') and seconds (") | | |
|---|---|---|---|---|
| Transfluthrin | Flu-fenoxuron | PVC | glazed tiles | unglazed tiles |
| — | 0.01 | 2 h 0% | 2 h 0% | 2 h 0% |
| 0.05 | — | 4'00/11'50 h | 3'50"/7'10" | 4'30"/10'30" |
| 0.05 | 0.01 | 2'40"/14'00" | 2'20"/3'30" | 3'30"/10'00" |
| 0.05 | 0.005 | 3'50"/12'50" | 2'20"/6'20" | 4'50/11'20" |
| 0.05 | 0.0025 | 1'50"/10'10" | 2'00"/5'30" | 2'10"/5'10" |
| — | — | 2 h 0% | 2 h 0% | 2 h 0% |

The experiments showed that flufenoxuron alone, as was to be expected, showed virtually no effect against both cockroach species within the test time of 2 hours.

If transfluthrin was combined with flufenoxuron in water-based spray cans, a distinct to significant better effect of the combinations compared with the transfluthrin monospray can (Table 11) resulted against German cockroaches on all surfaces tested.

Even with oriental cockroaches, in most cases a distinctly better effect was achieved by the combination spray cans, which was particularly true of PVC and glazed tiles (Table 12).

These improvements in action are obviously caused by synergistic effects of the flufenoxuron.

What is claimed is:

1. An insecticidal or acaricidal composition a synergistic effective amount therefor of a combination of transfluthrin and flufenoxuron.

2. The composition according to claim 1, which comprises 0.05% by weight of transfluthrin and 0.0025–0.01% by weight of flufenoxuron, the % by weight in each case being based on the weight of the composition.

3. The composition according to claim 1 which is a spray formulation.

4. The composition according to claim 1, which is a ULV, hot and cold mist, emulsion concentrate (EC), emulsion concentrate based on water (EW) or wettable powder (WP).

5. A method for controlling insects or acarids, said method comprising applying to the insects or acarids or their habitat an effective amount therefor of a composition according to any one of claims 3, 4, 1 or 2.

* * * * *